United States Patent

Tijer Miquel et al.

Patent Number: 5,208,393
Date of Patent: May 4, 1993

[54] PROCESS FOR THE MANUFACTURE OF CHLOROFORM

[75] Inventors: Emilio Tijer Miquel, Barcelona; José M. Sule Gimenez, Premia de Mar; Antonio Cortes Arroyo, Madrid; Xose L. Seoane Gomez, Madrid; Adolfo Arcoya Martin, Madrid, all of Spain

[73] Assignee: Ercros, S.A., Barcelona, Spain

[21] Appl. No.: 741,396

[22] PCT Filed: Dec. 13, 1990

[86] PCT No.: PCT/ES90/00047
§ 371 Date: Aug. 2, 1991
§ 102(e) Date: Aug. 2, 1991

[87] PCT Pub. No.: WO91/09827
PCT Pub. Date: Jul. 11, 1991

[30] Foreign Application Priority Data

Dec. 22, 1989 [ES] Spain ................... P 8904342

[51] Int. Cl.$^5$ ............ C07C 19/04; C07C 19/00; C07C 17/24; C07C 17/26
[52] U.S. Cl. ............ 570/101; 570/230; 570/237
[58] Field of Search ........................ 570/101

[56] References Cited

U.S. PATENT DOCUMENTS 5,097,081  3/1992  Correia et al. ............ 570/101

Primary Examiner—Joseph E. Evans
Attorney, Agent, or Firm—Michael J. Striker

[57] ABSTRACT

A process for the manufacture of chloroform by catalytic hydrogenolysis of carbon tetrachloride in liquid phase, wherein liquid phase carbon tetrachloride is reacted with hydrogen gas or a gas containing molecular hydrogen, at a pressure below 8,000 kPa and at a temperature below 250° C., in the presence of a catalyst formed by a metal selected from the group consisting of palladium, rhodium, ruthenium and platinum, deposited on a substrate and held in suspension in the liquid.

31 Claims, No Drawings

PROCESS FOR THE MANUFACTURE OF CHLOROFORM

BACKGROUND OF THE INVENTION

This invention relates to a process for the preparation of chloroform ($CHCl_3$), starting out from carbon tetrachloride ($CCl_4$)

There are references in the literature concerning several methods for reducing the halogen content of a range of organohalogenated compounds. Nevertheless, the majority are impractical and of no commercial interest because of their excessive sophistication.

As a result of the declining market for carbon tetrachloride, there is a growing excess of this product. In view of this situation, researchers are trying to revalue this product by searching for methods allowing it to be used as a raw material for the manufacture of chloroform, the market demand for which is, on the contrary, growing.

Thus, the Dow Chemical Co. U.S. Pat. No. 2,886,605 of 1959 teaches a method of hydrodehalogenation of polyhalogenated hydrocarbons, using a cuprous chloride catalyst in a fluidized bed. The greatest drawback of this method for commercial exploitation is that it is run at so high temperatures (350° C. to 550° C.) that such an abundant carbonization occurs that it becomes necessary continuously or very frequently to regenerate the catalyst.

Another Dow Chemical Co. patent (U.S. Pat. No. 3,579,596 of 1971) teaches a process for producing chloroform from gas phase carbon tetrachloride, using a fixed catalyst bed of platinum on a substrate. This method, nevertheless, suffers from serious limitations, for example, that a) the need to use excessively high amount of hydrogen relative to a stoichiometric amount encourages the production of methane and, furthermore, extraordinarily hinders the recovery of the reaction products, and b) The reaction is highly exothermic ($\Delta H = -22.70$ kcal/mol, at 400 K, for a 100% theoretical selectivity of chloroform production), making it very hard to control the temperature. According to trials carried out by the inventors, hot spots are formed in the catalyst in the gas phase process, encouraging the formation of free radicals which, in turn, give rise to the formation of heavy polychlorinated compounds. When these are deposited on the catalyst surface they almost immediately and irreversibly deactivate it.

SUMMARY OF THE INVENTION

According to the present invention, liquid carbon tetrachloride is reacted with hydrogen gas or with a molecular hydrogen-containing gas, at a pressure below 8,000 kPa and at a temperature below 250° C. in the presence of a catalyst comprising a metal deposited on a powdered substrate. The metal is palladium, rhodium, ruthenium or platinum. The reaction takes place with the catalyst in suspension in the liquid.

According to the invention, the reaction is conducted in liquid phase, with a supported powdered metal catalyst in suspension in contact with the molecular hydrogen. The catalyst active component is a metal selected from the group formed by palladium, rhodium, ruthenium and platinum. Thus, under the conditions to be described hereinafter, the carbon tetrachloride is converted into chloroform, at low temperature, with high conversion and selectivity rates.

The process has proved to be particularly effective when the chosen metal is palladium.

The present inventors have discovered, and this is a very important advantage of this invention, that when the reaction is conducted under the abovementioned conditions, the drawbacks mentioned above are avoided.

A further important advantage of the process of the invention is that it allows the temperature to be easily controlled, thereby avoiding the formation of chlorinated polymers and it also allows the activity of the catalyst to be maintained for sufficient time to make the process commercially profitable.

Yet a further important advantage of the process of the invention over other known processes, is that the liquid phase system allows a low excess of hydrogen to be used, representing an undeniable financial saving. Furthermore, under these conditions, the production of methane and other unprofitable by-products is avoided, this being yet a further advantage of the new process.

The catalyst used in the process of the invention is formed by a metal selected from the group formed by palladium, rhodium, ruthenium and platinum deposited on a suitable substrate, such as carbon, silica, alumina, etc. Thus, a catalyst having shown itself to have a high activity and selectivity together with high stability is metallic palladium deposited on activated carbon having a large surface area.

To prepare the catalyst, the metal may be deposited on the substrate by any of the methods regularly used for this purpose, such as, for example, impregnation with or without an excess of solution, precipitation, etc, using aqueous or organic solvents.

As precursor salts of the metal, chlorides, ammoniacal chlorides, organic complexes, nitrates, acetates, etc. may be used, both in the commercial form thereof and as a result of dissolving the metal in an appropriate solvent.

Once the precursor has been deposited on the substrate, it is allowed to dry at room temperature for three hours and subsequently at a temperature ranging from 100° C. to 140° C. for the time required to remove the residual water.

Thereafter the catalyst is reduced to the metallic state in the presence of a molecular hydrogen-containing gas or an appropriate reducing gas such as hydrazine, methane, etc. To improve the activity, the reduction may be effected at temperatures ranging from 100° C. to 500° C., preferably from 150° C. to 450° C., the range of 200° C. to 300° C. being most advantageous when the metal is palladium. The reduction may be effected at atmospheric pressure or at a higher pressure. The optimum duration ranges from 1 to 4 hours and the hydrogen flow from 200 to 1,000 liters/hour per kg of catalyst, although an amount of hydrogen ranging from 2 to 5 times the amount required to reduce all the metal is sufficient.

The metal content of the catalyst may range from 0.1 to 5 wt % relative to the total weight of the final catalyst, although the preferred range is from 0.1 to 2 wt %.

For the very nature of the process of the invention, a high solid-liquid contact area is required, whereby it is desirable to use the catalyst in powder form, with a particle size not above 0.45 mm and preferably of less than 0.2 mm.

Also, to achieve an effective gas-solid-liquid contact and to obtain a maximum performance, it is necessary to remove the physical obstacles to the diffusion of the hydrogen in the gas-liquid and liquid-solid interfaces and to establish a control system of the chemical kinetics. Thus, any conventional mechanical stirring system may be used, or advantage may be taken of the linear velocity of the hydrogen itself, adequately dispersed in the liquid, to create the necessary turbulence.

For the preparation of the catalyst, the substrate may initially have the form of pellets, grains or extrudates, to be subsequently reduced to the selected particle size. Nevertheless, the metal precursor may also be incorporated directly on the powdered substrate.

To summarize, as said above, this new process of manufacturing chloroform by catalytic hydrogenolysis of carbon tetrachloride is characterized essentially in being conducted in the liquid phase, containing the appropriate amount of powdered catalyst in suspension, in the presence of hydrogen at an appropriate temperature and pressure.

OPERATING CONDITIONS OF THE PROCESS OF THE INVENTION

The process may be operated indifferently batchwise, semi-continuously or continuously. For batchwise production, a stirred autoclave type reactor may be used, containing the liquid carbon tetrachloride and catalyst charge, in the appropriate proportions. Hydrogen is allowed to flow in up to the set pressure, the mass is heated up to the operating temperature and is held under these conditions for the time required to achieve the desired conversion. At the end of this time, the reaction products are discharged and separated. Both the unreacted reactant and the catalyst may be reused.

If it is wished to conduct the reaction on a semi-continuous basis, either an autoclave type reactor or a tubular reactor may be used. The liquid and the catalyst are charged in the required proportions and the required hydrogen flow is provided. At the same time, the working temperature and pressure are adjusted. If the process is carried out in a laboratory, the gaseous effluent of the reactor, containing $H_2$, hydrogen chloride, methane and chlorinated hydrocarbons, is fed through a water absorption column where the hydrogen chloride is retained. Thereafter, the chlorinated products are condensed at a desirable temperature and the main reaction product, i.e. the chloroform is separated from them, for example, by distillation. If necessary, the gas flow and the unreacted reactant may be recycled. The apparatus is provided with a cyclone and/or filter to recover any entrained catalyst and return it to the reactor. The observed losses of catalyst are minimal. Once the desired conversion has been attained, the reactor content, after removal of the catalyst, is sent to distillation to recover the chloroform. The unreacted carbon tetrachloride is recycled to the reactor.

The process may be carried out equally well reversing the order described above for the chlorinated product condensation and the hydrogen chloride absorption. This last operating method is more appropriate for application in an industrial plant.

When operating continuously, the same operating method is used as in the above described semi-continuous method, except that in this case the carbon tetrachloride is also supplied continuously in liquid phase at the required flow rate. The two reactor effluents, gas and liquid, are separated and processed as in the previously described semi-continuous operation.

The high activity shown by the catalyst used in the process of the invention, together with the reaction being carried out in the liquid phase, not only allows low temperatures to be used, but also an excellent control of the temperature within the reactor to be maintained, the gradients not normally exceeding the values of $\Delta T = \pm 5°$ C. Thus, hot spots are eliminated, the life of the catalyst is extended and high selectivity rates are obtained for the preparation of the desired products. As said above, this is one of the great advantages of the invention and a notable improvement over the processes carrying out the same reaction but in the gas phase. Thus, the reaction may be carried out with satisfactory yields at temperatures ranging from 100° C. to 300° C., although temperatures ranging from 120° C. to 160° C. are preferable.

The reaction is conducted advantageously at pressures above atmospheric pressure. Excessively high pressure do not provide substantial advantages to the reaction kinetics and increase the production costs. Therefore, the operating pressure should range from 500 to 8,000 kPa and preferably from 1,500 to 5,000 kPa.

The hydrogen supply should be sufficiently selective to product the desired reaction, i.e., the preparation of chloroform. This reaction is:

$$CCl_4 + H_2 \rightarrow CHCl_3 + HCl$$

It is essential that the reaction should not be controlled by the availability of the hydrogen in the liquid phase, or by the desorption of the hydrogen chloride produced, which is guaranteed by maintaining always a slight excess of hydrogen in the gas exhaust and good mechanical stirring. This excess must, obviously, be higher if the hydrogen flow is also used as stirring system for the liquid and the catalyst in the reactor. Tests have shown that even using this method of stirring in a semi-continuous reactor, an $H_2/CCl_4$ molar ratio of less than 2/1 is sufficient to obtain molar conversions of carbon tetrachloride of over 85% and chloroform preparation selectivity rates of about the same order, after a period ranging from 2 to 4 hours operation, depending on the experimental conditions. This low hydrogen consumption is another important financial incentive of the process of the present invention, not provided by other known processes.

Another parameter determining the commercial profitability of this process is the relatively low content of metal used as active component, both in the catalyst composition and in the catalyst/chlorinated reactant (wt/wt) ratio used in the reactor. For low values of this ratio, the productivity increases more than linearly on increasing it, since thereby the amount of catalyst particles in the slurry and, therefore, the contact area of the catalyst, also increase. It is well known that the reaction rate is proportional to this area. Nevertheless, higher values, competition occurs for the $H_2$ among the catalyst particles, whereby there is a reduction of the effective amount of catalyst, saturation is reached and the activity per gram practically no longer increases. When the catalyst element is palladium, ratios ranging from 0.1/100 and 5/100 (wt/wt), more preferably 0.5/100 to 2.5/100, have been found to be acceptable for the catalyst/$CCl_4$ ratio. The highest rates of chloroform production, expressed as kg $CHCl_3$/hour per kg palladium are obtained with these ratios.

EXAMPLES

The following Examples, given without any limitative effect, serve to provide a better understanding of the invention.

EXAMPLE 1

This Example relates to a way of preparing a palladium catalyst, using activated carbon of 1,200 m²/g as substrate, in the form of pellets of about 3 mm diameter by 4 mm long. The retention volume or maximum water absorption volume is 95 cm³/g.

1.0 g of powered palladium metal was dissolved in 7.0 ml of aqua regia at 80° C. Once dissolved, it was dried and the residue was dissolved in 5.0 cm³ of 12N hydrochloric acid, at room temperature. The resulting solution was topped up to 95 cm³ with distilled water and poured over 100 g of carbon pellets.

The pellets were thoroughly stirred to produce a homogenous absorption of the solution, it was allowed to dry at room temperature for three hours and then at 120° C. for twelve hours. Subsequently, it was reduced at 250° C. at atmospheric pressure, with 500 l/hour hydrogen per kg catalyst being blown over for three hours. It was allowed to cool to room temperature under hydrogen flow. The catalyst contained 1 wt % of palladium metal.

Subsequently, for use in the liquid phase reaction, the catalyst pellets were reduced to a size of below 0.177 mm.

EXAMPLE 2

This Example relates to the preparation of chloroform ($CHCl_3$). 2,072 g of liquid carbon tetrachloride were charged into a stainless steel tubular reactor, 1.25 m high×4 cm inside diameter, without mechanical stirring, and 24.89 g of catalyst prepared as per Example 1 were added. After purging the air, the hydrogen flow was opened and was adjusted to give permanently 1 l/min $H_2$ in the exhaust. The hydrogen was fed in through the bottom of the reactor, was diffused through a perforated plate and, further to being used as reactant, it was also used to stir the liquid and the solid. The reactor was heated to 160° C. and the pressure was adjusted to 3,000 kPa. After one hour (t=1 hour) an 86.6% carbon tetrachloride conversion to chloroform, with a 77.6% molar selectivity (S) was obtained, representing a productivity rate (P) of 2,762 kg $CHCl_3$/hour per kg palladium.

The selectivity (S) is defined as the number of moles of carbon tetrachloride converted into product, divided by the total number of moles of carbon tetrachloride reacted multiplied by 100.

The main by-products obtained were:
hexachloroethane, with selectivity: $S(C_2Cl_6)=1.2\%$.
tetrachloroethylene, with selectivity: $S(C_2Cl_4)=14.8\%$
methane, with selectivity: $S(CH_4)=3.9\%$.

The complements to 100 of the sum of the selectivities of carbon tetrachloride and the above main by-products correspond to small amounts of other by-products, such as ethane, trichloroethane, pentachloroethane and traces of others.

EXAMPLE 3

In an experiment conducted with the same catalyst, the same catalyst/carbon tetrachloride ratio and the same hydrogen flow in the exhaust and protocol as described in Example 2, but at 140° C. and 1,500 kPa, the following results were obtained:

| After 2 hours operation (t = 2 hours) |
| --- |
| Conversion ($CCl_4$) = 42.9% |
| S ($CHCl_3$) = 73.9% |
| P ($CHCl_3$) = 1,024 kg/hour per kg palladium |
| S ($C_2Cl_6$) = 18.0% |
| S ($C_2Cl_4$) = 2.6% |
| S ($CH_4$) = 0.7% |
| After 4 hours operation (t = 4 hours) |
| Conversion ($CCl_4$) = 68.2% |
| S ($CHCl_3$) = 69% |
| P ($CHCl_3$) = 761 kg/hour per kg palladium |
| S ($C_2Cl_6$) = 21.0% |
| S ($C_2Cl_4$) = 4.8% |
| S ($CH_4$) = 1.8% |

EXAMPLE 4

2,072 g of liquid $CCl_4$ and 24.86 g of a catalyst prepared according to Example 1, but containing 0.5% wt palladium were charged in the reactor described in Example 2. When operating at 140° C. and 1,500 kPa, with 1 ./min $H_2$ in the exhaust, the following results were obtained:

| t = 2 hours |
| --- |
| Conversion ($CCl_4$) = 34.6% |
| S ($CHCl_3$) = 78.5% |
| P ($CHCl_3$) = 1,785 kg/hour per kg palladium |
| S ($C_2Cl_6$) = 13.3% |
| S ($CH_4$) = 3.2% |
| t = 4 hours |
| Conversion ($CCl_4$) = 69% |
| S $CHCl_3$) = 74.9% |
| P ($CHCl_3$) = 1,671 kg/hour per kg palladium |
| S ($C_2Cl_6$) = 16.5% |
| S ($C_2Cl_4$) = 3.0% |
| S ($CH_4$) = 2.9% |

EXAMPLE 5

In an experiment conducted under the same conditions as in Example 4, but containing 51.8 g of catalyst, i.e. a catalyst/$CCl_4$ ratio of 2.5/100 (wt/wt), the following results were obtained:

| t = 2 hours |
| --- |
| Conversion ($CCl_4$) = 78.1% |
| S ($CHCl_3$) = 85.9% |
| P ($CHCl_3$) = 2,083 kg/hour per kg palladium |
| S ($C_2Cl_6$) = 8.1% |
| S ($C_2Cl_4$) = 3.2% |
| S ($CH_4$) = 1.0% |
| t = 4 hours |
| Conversion ($CCl_4$) = 99.9% |
| S ($CHCl_3$) = 88.0% |
| P ($CHCl_3$) = 1,366 kg/hour per kg palladium |
| S ($C_2Cl_6$) = 0.3% |
| S ($C_2Cl_4$) = 6.5% |
| S ($CH_4$) = 1.7% |

EXAMPLE 6

Following the method of Example 1, a palladium catalyst containing 1 wt % of metal was prepared, using as substrate a different activated carbon having a specific area of 820 m³/g and 78% retaining volume.

EXAMPLE 7

An experiment was conducted with the catalyst prepared as per Example 6 with the same equipment as in the previous Examples and under the same experimental conditions as in Example 3, the following results being obtained:

| t = 2 hours |
| --- |
| Conversion ($CCl_4$) = 39.4% |
| S ($CHCl_3$) = 80.8% |
| P ($CHCl_3$) = 1,028 kg/hour per kg palladium |
| S ($C_2Cl_6$) = 9.5% |
| S ($C_2Cl_4$) = 1.0% |
| S ($CH_4$) = 3.1% |
| t = 4 hours |
| Conversion ($CCl_4$) = 72.3% |
| S ($CHCl_3$) = 77% |
| P ($CHCl_3$) = 901 kg/hour per kg palladium |
| S ($C_2Cl_6$) = 8.0% |
| S ($C_2Cl_4$) = 2.2% |
| S ($CH_4$) = 3.2% |

EXAMPLE 8

An experiment was conducted with a catalyst prepared according to Example 6, but containing 0.5 wt % palladium, semi-continuously, in a mechanically stirred reactor, at 140° C. temperature, 1,500 kPa pressure, with a catalyst/carbon tetrachloride ratio of 1.2/100 (wt/wt) and a hydrogen flow at the exhaust of 1 l/min. The following results were obtained:

| t = 2 hours |
| --- |
| Conversion ($CCl_4$) = 58.1% |
| S ($CHCl_3$) = 76.4% |
| P ($CHCl_3$) = 2,871 kg/hour per kg palladium |
| S ($C_2Cl_6$) = 16.3% |
| S ($C_2Cl_4$) = 2.9% |
| S ($CH_4$) = 3.6% |
| t = 4 hours |
| Conversion ($CCl_4$) = 94.8% |
| S ($CHCl_3$) = 79.6% |
| P ($CHCl_3$) = 2,441 kg/hour per kg palladium |
| S ($C_2Cl_6$) = 7.0% |
| S ($C_2Cl_4$) = 9.6% |
| S ($CH_4$) = 3.1% |

EXAMPLE 9

This Example relates to a way of preparing a rhodium (Rh) catalyst.

A rhodium (Rh) catalyst was prepared by dissolving in distilled water the amount of rhodium trichloride ($RhCl_3$) necessary for the final catalyst to contain 1.6 wt % of rhodium metal relative to the total catalyst weight. Distilled water was added to the resulting solution to complete a volume equal to the retention volume of the carbon used in Example 1. After impregnating the substrate with this solution, it was dried at 120° C. for twelve hours and was then reduced at 150° C., under flowing hydrogen, for two hours.

EXAMPLE 10

An experiment was conducted with the catalyst prepared according to Example 9 under the same conditions as described in Example 8, but using a catalyst/carbon tetrachloride ratio of 1.0/100 (wt/wt). The following results were obtained:

| t = 2 hours |
| --- |
| Conversion ($CCl_4$) = 4.8% |
| S ($CHCl_3$) = 32.0% |
| P ($CHCl_3$) = 37.7 kg/hour per kg rhodium |
| S ($C_2Cl_6$) = 61.6% |
| S ($C_2Cl_4$) = 6.1% |
| S ($CH_4$) = Traces |

EXAMPLE 11

This Example relates to a way of preparing a ruthenium (Ru) catalyst.

A catalyst containing 1.6 wt % of ruthenium (Ru) was prepared from ruthenium trichloride ($RuCl_3$, using the same method and substrate as in Example 9, except that the reduction was conducted at 250° C.

EXAMPLE 12

An experiment was conducted with the catalyst described in Example 11, under the same conditions as Example 10, with the following results being obtained:

| t = 2 hours |
| --- |
| Conversion ($CCl_4$) = 10% |
| S ($CHCl_3$) = 9% |
| P ($CHCl_3$) = 20.7 kg/hour per kg ruthenium |
| S ($C_2Cl_6$) = 86.0% |
| S ($C_2Cl_4$) = 3.0% |
| S ($CH_4$) = 2.0% |

EXAMPLE 13

This Example relates to a way of preparing a platinum (Pt) catalyst.

A platinum catalyst was prepared using powdered silica of 600 $m^2$/g specific area and 3.0 $cm^3$/g specific retention volume as substrate. 1 g of hexachloroplatinic acid ($H_2PtCl_6.6H_2O$) was dissolved in distilled water to complete a volume of 113 $cm^3$. The solution was poured over 37.5 g of substrate. Once the solid was well impregnated, it was dried at 120° C. for 12 hours, was calcined at 500° C. under flowing air for two hours and was reduced at 450° C. under flowing hydrogen for two hours. The final catalyst contained 1 wt % of platinum metal.

EXAMPLE 14

An experiment was conducted with the catalyst prepared according to Example 13 under the same conditions as described in Example 8, with the following results being obtained:

| t = 2 hours |
| --- |
| Conversion ($CCl_4$) = 2.1% |
| S ($CHCl_3$) = 30% |
| P ($CHCl_3$) = 17.5 kg/hour per kg platinum |
| S ($C_2Cl_6$) = 70% |
| S ($CH_4$) = 0% |

EXAMPLE 15

Example 15 also deals with the preparation of a platinum catalyst.

Following the method of Example 13, a platinum catalyst was prepared, but using the activated carbon of Example 6. After impregnation and drying, the catalyst was reduced directly with $H_2$ at 450° C., without prior calcination. The final catalyst contained 1 wt % of platinum metal.

EXAMPLE 16

An experiment was conducted with the catalyst of Example 15, under the conditions described in Example 8, with the following results being obtained:

| t = 1 hour |
| --- |
| Conversion ($CCl_4$) = 61.5% |
| S ($CHCl_3$) = 75.3% |
| P ($CHCl_3$) = 2,992 kg/hour per kg platinum |
| S ($C_2Cl_6$) = 16.4% |
| S ($C_2Cl_4$) = 6.2% |
| S ($CH_4$) = 2.0% |

The results given in the foregoing Examples show that the process of the invention is sufficiently versatile to be adaptable to various industrial situations. In fact, by varying the operative conditions, different combinations of carbon tetrachloride conversion and chloroform productivity rates may be obtained, in all cases with a relatively small amount of by-products. In each case, an analysis of the different operating power, separation and recycling costs, together with the raw material and product market prices, will allow the most profitable production scheme to be adopted.

We claim:

1. A process for manufacture of chloroform by catalytic hydrogenolysis of carbon tetrachloride, comprising the steps of reacting liquid carbon tetrachloride with a hydrogen-containing member selected from the group consisting of hydrogen gas and gases containing molecular hydrogen at a pressure below 8,000 kPa and at a temperature below 250° C., in the presence of a catalyst, said catalyst comprising a metal deposited on a powdered substrate, and said catalyst being held in suspension in the liquid carbon tetrachloride, said metal being selected from the group consisting of palladium, rhodium, ruthenium and platinum.

2. The process according to claim 1, wherein the powdered substrate is selected from the group consisting of activated carbon, silica and alumina powders.

3. The process according to claim 1, further comprising impregnating the substrate with a solution of at least one slat of the metal selected as active component of the catalyst.

4. The process according to claim 3, wherein the salt is selected from the group consisting of inorganic salts and organic salts.

5. The process according to claim 3, wherein the solution is an organic solution.

6. The process according to claim 3, wherein the solution is an aqueous solution.

7. The process according to claim 1, further comprising precipitating a precursor substance containing the metal selected as active component of the catalyst onto the substrate.

8. The process according to claim 1, wherein said reacting is conducted batchwise with a charge of liquid carbon tetrachloride containing the catalyst in suspension, and further comprising supplying said hydrogen-containing member up to a working pressure.

9. The process according to claim 1, wherein said reacting is conducted semi-continuously with a charge of liquid carbon tetrachloride containing the catalyst in suspension, and further comprising supplying said hydrogen-containing member up to a working pressure.

10. The process according to claim 1, wherein said reacting is conducted continuously with the liquid carbon tetrachloride and the hydrogen-containing member being supplied continuously, and further comprising suspending the catalyst in the liquid carbon tetrachloride.

11. The process according to claim 1, further comprising stirring the liquid carbon tetrachloride mechanically.

12. The process according to claim 1, further comprising stirring the liquid carbon tetrachloride by action of a flow of the hydrogen-containing member.

13. The process according to claim 1, wherein the reacting occurs in one of an autoclave and a tubular reactor.

14. A process for manufacture of chloroform by catalytic hydrogenolysis of carbon tetrachloride, comprising the steps of reacting liquid carbon tetrachloride with a hydrogen-containing member selected from the group consisting of hydrogen gas and gases containing molecular hydrogen at a pressure below 8,000 kPa and at a temperature below 250° C., in the presence of a catalyst, said catalyst comprising a metal deposited on a powdered substrate, and said catalyst being held in suspension in the liquid carbon tetrachloride, said metal being selected from the group consisting of palladium, rhodium, ruthenium and platinum, and wherein the catalyst and the liquid carbon tetrachloride are present in a weight ratio of from 0.1/100 to 5/100 during the reacting.

15. The process according to claim 14, wherein the weight ratio is from 0.5/100 to 2.5/100.

16. The process according to claim 1, wherein the hydrogen-containing member and the liquid carbon tetrachloride are present in a weight ratio of one to two times a stoichiometric ratio for a reaction of the hydrogen-containing member with the carbon tetrachloride.

17. A process for manufacture of chloroform by catalytic hydrogenolysis of carbon tetrachloride, comprising the steps of reacting liquid carbon tetrachloride with a hydrogen-containing member selected form the group consisting of hydrogen gas and gases containing molecular hydrogen at a pressure below 8,000 kPa and at a temperature below 250° C., in the presence of a catalyst, said catalyst comprising a metal deposited on a powdered substrate, and said catalyst being held in suspension in the liquid carbon tetrachloride, said metal being selected from the group consisting of palladium, rhodium, ruthenium and platinum, and wherein the temperature during said reacting is from 100 C. to below 250° C.

18. The process according to claim 17, wherein the temperature during said reacting is from 120° C. to 160° C.

19. A process for manufacture of chloroform by catalytic hydrogenolysis of carbon tetrachloride, comprising the steps of reacting liquid carbon tetrachloride with a hydrogen-containing member selected from the group consisting of hydrogen gas and gases containing molecular hydrogen at a pressure below 8,000 kPa and at a temperature below 250° C., in the presence of a catalyst, said catalyst comprising a metal deposited on a powdered substrate, and said catalyst being held in suspension in the liquid carbon tetrachloride, said metal being selected from the group consisting of palladium, rhodium, ruthenium and platinum, and wherein the pressure during the reacting is from 500 kPa to below 8,000 kPa.

20. The process according to claim 19, wherein the pressure during the reacting is from 1,500 kPa to 5,000 kPa.

21. A process for manufacture of chloroform by catalytic hydrogenolysis of carbon tetrachloride, comprising the steps of reacting liquid carbon tetrachloride with a hydrogen-containing member selected from the group consisting of hydrogen gas and gases containing molecular hydrogen at a pressure below 8,000 kPa and at a temperature below 250° C., in the presence of a catalyst, said catalyst comprising palladium deposited on a powdered substrate, and said catalyst being held in suspension in the liquid carbon tetrachloride.

22. The process according to claim 21, further comprising dissolving the palladium in a solvent to form a palladium salt and impregnating the substrate with the palladium salt.

23. The process according to claim 22, wherein the palladium salt is one of an inorganic palladium salt and an organic palladium salt.

24. The process according to claim 21, wherein the catalyst contains from 0.1 to 5.0% by weight of the palladium relative to a total catalyst weight.

25. The process according to claim 21, wherein the catalyst contains from 0.1 to 2.0% by weight of the palladium relative to a total catalyst weight.

26. The process according to claim 22, further comprising reducing the palladium salt to palladium metal with hydrogen gas at a temperature ranging from 100° C. to 500°.

27. The process according to claim 26, wherein the temperature of said reducing is from 200° C. to 300° C.

28. The process according to claim 1, wherein the metal is the rhodium.

29. The process according to claim 1, wherein the metal is the ruthenium.

30. The process according to claim 1, wherein the metal is the platinum.

31. A process for manufacture of chloroform by catalytic hydrogenolysis of carbon tetrachloride, comprising the steps of:

a) impregnating a powdered substrate with at least one palladium salt by treating the powdered substrate with the at least one palladium salt in a solvent;

b) reducing the at least one palladium salt impregnated on the powdered substrate to form a catalyst containing palladium metal, said reducing being carried out with hydrogen gas at a temperature ranging from 100° C. to 500° C. so that the catalyst contains from 0.10 to 5.0% by weight of the palladium metal; and c) reacting liquid carbon tetrachloride with a hydrogen-containing member selected from the group consisting of hydrogen gas and gases containing molecular hydrogen at a pressure from 500 to below 8,000 kPa and at a temperature from 100° C. to below 250° C. in the presence of the catalyst to form the chloroform, wherein the catalyst and the liquid carbon tetrachloride are present in a weight ratio of 0.1/100 to 5/100 during the reacting.

* * * * *